US010244948B2

(12) United States Patent
Pham et al.

(10) Patent No.: US 10,244,948 B2
(45) Date of Patent: Apr. 2, 2019

(54) STATISTICAL HEART RATE MONITORING FOR ESTIMATING CALORIE EXPENDITURE

(71) Applicant: Apple Inc., Cupertino, CA (US)

(72) Inventors: Hung A. Pham, Cupertino, CA (US); Craig Mermel, Cupertino, CA (US); Richard Channing Moore, III, San Francisco, CA (US); Karthik Jayaraman Raghuram, Cupertino, CA (US); Adeeti Ullal, Cupertino, CA (US); Alexander Singh Alvarado, Cupertino, CA (US); Xing Tan, Cupertino, CA (US)

( * ) Notice: Subject to any disclaimer, the term of this patent is extended or adjusted under 35 U.S.C. 154(b) by 218 days.

(21) Appl. No.: 15/061,653

(22) Filed: Mar. 4, 2016

(65) Prior Publication Data

US 2016/0256058 A1  Sep. 8, 2016

Related U.S. Application Data

(60) Provisional application No. 62/129,510, filed on Mar. 6, 2015.

(51) Int. Cl.
*A61B 5/02* (2006.01)
*A61B 5/0205* (2006.01)
(Continued)

(52) U.S. Cl.
CPC ........ *A61B 5/0205* (2013.01); *A61B 5/02438* (2013.01); *A61B 5/1118* (2013.01);
(Continued)

(58) Field of Classification Search
CPC . A61B 5/0205; A61B 5/02438; A61B 5/1118; A61B 5/4866
See application file for complete search history.

(56) References Cited

U.S. PATENT DOCUMENTS 4,566,461 A   1/1986 Lubell et al.
5,158,093 A   10/1992 Shvartz et al.
(Continued)

FOREIGN PATENT DOCUMENTS

GB   2465824 A       6/2010
WO   2010/090867 A2  8/2010
WO   2011/105914 A1  9/2011

OTHER PUBLICATIONS

Wang et al., "Time constant of heart rate recovery after low level exercise as a useful measure of cardiovascular fitness," Conf. Proc. IEEE Eng. Meda Biol. Soc., vol. 1, pp. 1799-1802 : (2006).
(Continued)

*Primary Examiner* — Eric D. Bertram
(74) *Attorney, Agent, or Firm* — DLA Piper LLP US

(57) ABSTRACT

Systems and methods are disclosed for tracking physiological states and parameters for calorie estimation. A start of an exercise session associated with a user of a wearable computing device is determined. Heart rate data is measured for a first period of time. An onset heart rate value of the user is determined based on the measured heart rate data, the onset heart rate value associated with a lowest valid heart rate measured during the first period of time. A resting heart rate parameter (RHR) of a calorimetry model is associated with at least one of the onset heart rate value, a preset RHR, and an RHR based on user biometric data. Energy expenditure of the user during a second period of time is estimated based on the calorimetry model and a plurality of heart rate measurements obtained by the wearable computing device during the second period of time.

20 Claims, 6 Drawing Sheets

(51) Int. Cl.
- *A61B 5/024* (2006.01)
- *A61B 5/11* (2006.01)
- *A61B 5/00* (2006.01)

(52) U.S. Cl.
CPC .... *A61B 5/4866* (2013.01); *A61B 2560/0223* (2013.01); *A61B 2562/0219* (2013.01)

(56) References Cited

U.S. PATENT DOCUMENTS

| | | | |
|---|---|---|---|
| 6,013,008 A | 1/2000 | Fukushima | |
| 6,059,724 A | 5/2000 | Campbell et al. | |
| 6,582,380 B2 | 6/2003 | Kazlausky et al. | |
| 6,687,535 B2 | 2/2004 | Hautala et al. | |
| 6,837,827 B1 | 1/2005 | Lee et al. | |
| 7,254,516 B2 | 8/2007 | Case et al. | |
| 7,467,060 B2 | 12/2008 | Kulach et al. | |
| 7,534,206 B1 | 5/2009 | Lovitt et al. | |
| 7,690,556 B1 | 4/2010 | Kahn et al. | |
| 7,771,320 B2 | 8/2010 | Riley et al. | |
| 7,805,149 B2 | 9/2010 | Werner et al. | |
| 7,841,967 B1 | 11/2010 | Kahn et al. | |
| 8,290,480 B2 | 10/2012 | Abramson et al. | |
| 8,483,775 B2 | 7/2013 | Buck et al. | |
| 8,589,174 B2 | 11/2013 | Nelson et al. | |
| 8,892,391 B2 | 11/2014 | Tu et al. | |
| 8,894,576 B2 | 11/2014 | Alwan et al. | |
| 9,413,871 B2 | 8/2016 | Nixon et al. | |
| 9,526,430 B2 | 12/2016 | Srinivas et al. | |
| 2002/0019585 A1* | 2/2002 | Dickinson | A61B 5/02438 600/300 |
| 2003/0032460 A1 | 2/2003 | Cannon et al. | |
| 2004/0064061 A1 | 4/2004 | Nissila | |
| 2005/0107723 A1 | 5/2005 | Wehman et al. | |
| 2006/0217231 A1 | 9/2006 | Parks et al. | |
| 2007/0100666 A1 | 5/2007 | Stivoric et al. | |
| 2007/0275825 A1 | 11/2007 | O'Brien | |
| 2008/0096726 A1 | 4/2008 | Riley et al. | |
| 2008/0214360 A1 | 9/2008 | Stirling et al. | |
| 2009/0009320 A1 | 1/2009 | O'Connor et al. | |
| 2009/0043531 A1 | 2/2009 | Kahn et al. | |
| 2010/0130890 A1 | 5/2010 | Matsumura et al. | |
| 2010/0204952 A1 | 8/2010 | Irlam et al. | |
| 2010/0210953 A1 | 8/2010 | Sholder et al. | |
| 2010/0210975 A1 | 8/2010 | Anthony, III et al. | |
| 2010/0217099 A1 | 8/2010 | Leboeuf et al. | |
| 2010/0298656 A1 | 11/2010 | McCombie et al. | |
| 2011/0040193 A1 | 2/2011 | Seppanen et al. | |
| 2011/0054359 A1 | 3/2011 | Sazonov et al. | |
| 2011/0131012 A1 | 6/2011 | Czaja et al. | |
| 2011/0152695 A1 | 6/2011 | Granqvist et al. | |
| 2011/0195707 A1 | 8/2011 | Faerber et al. | |
| 2011/0238485 A1 | 9/2011 | Haumont et al. | |
| 2012/0083715 A1 | 4/2012 | Yuen et al. | |
| 2012/0172677 A1 | 7/2012 | Logan et al. | |
| 2012/0238832 A1 | 9/2012 | Jang et al. | |
| 2012/0296455 A1 | 11/2012 | Ohnemus et al. | |
| 2013/0023739 A1 | 1/2013 | Russell | |
| 2013/0096943 A1 | 4/2013 | Carey et al. | |
| 2013/0158686 A1 | 6/2013 | Zhang et al. | |
| 2013/0197377 A1 | 8/2013 | Kishi et al. | |
| 2013/0267794 A1 | 10/2013 | Fernstrom et al. | |
| 2014/0087708 A1 | 3/2014 | Kalita et al. | |
| 2014/0088444 A1 | 3/2014 | Saalasti et al. | |
| 2014/0107932 A1 | 4/2014 | Luna | |
| 2014/0109390 A1 | 4/2014 | Manning | |
| 2014/0167973 A1 | 6/2014 | Letchner et al. | |
| 2014/0172238 A1 | 6/2014 | Craine | |
| 2014/0197946 A1 | 7/2014 | Park et al. | |
| 2014/0200906 A1 | 7/2014 | Bentley et al. | |
| 2014/0207264 A1 | 7/2014 | Quy | |
| 2014/0213920 A1 | 7/2014 | Lee et al. | |
| 2014/0221854 A1 | 8/2014 | Wai | |
| 2014/0244071 A1 | 8/2014 | Czaja et al. | |
| 2014/0266789 A1 | 9/2014 | Matus | |
| 2014/0276127 A1 | 9/2014 | Ferdosi et al. | |
| 2014/0278139 A1 | 9/2014 | Hong et al. | |
| 2014/0278229 A1 | 9/2014 | Hong et al. | |
| 2014/0316305 A1 | 10/2014 | Venkatraman et al. | |
| 2015/0087929 A1 | 3/2015 | Rapoport et al. | |
| 2015/0088006 A1 | 3/2015 | Rapoport et al. | |
| 2015/0100141 A1 | 4/2015 | Hughes | |
| 2015/0119728 A1 | 4/2015 | Blackadar et al. | |
| 2015/0256689 A1 | 9/2015 | Erkkila et al. | |
| 2015/0260514 A1 | 9/2015 | Menelas et al. | |
| 2015/0345985 A1* | 12/2015 | Fung | G16H 40/63 702/160 |
| 2015/0374240 A1 | 12/2015 | Lee | |
| 2016/0021238 A1 | 1/2016 | Abramson et al. | |
| 2016/0057372 A1 | 2/2016 | Iwane et al. | |
| 2016/0058302 A1 | 3/2016 | Raghuram et al. | |
| 2016/0058329 A1 | 3/2016 | Srinivas et al. | |
| 2016/0058332 A1 | 3/2016 | Tan et al. | |
| 2016/0058333 A1 | 3/2016 | Arnold et al. | |
| 2016/0058356 A1 | 3/2016 | Raghuram et al. | |
| 2016/0058370 A1 | 3/2016 | Raghuram et al. | |
| 2016/0058371 A1 | 3/2016 | Singh et al. | |
| 2016/0058372 A1 | 3/2016 | Raghuram et al. | |
| 2016/0170998 A1 | 6/2016 | Frank et al. | |
| 2016/0206248 A1 | 7/2016 | Sartor et al. | |
| 2016/0269572 A1 | 9/2016 | Erkkila et al. | |
| 2016/0287177 A1 | 10/2016 | Huppert et al. | |
| 2017/0074897 A1 | 3/2017 | Mermel et al. | |
| 2017/0082649 A1 | 3/2017 | Tu et al. | |
| 2017/0094450 A1 | 3/2017 | Tu et al. | |
| 2017/0111768 A1 | 4/2017 | Smith et al. | |
| 2017/0188893 A1 | 7/2017 | Venkatraman et al. | |
| 2017/0202486 A1 | 7/2017 | Martikka et al. | |
| 2017/0259116 A1 | 9/2017 | Mestas | |
| 2017/0273619 A1 | 9/2017 | Alvarado et al. | |

OTHER PUBLICATIONS

Vella et al, Exercise After-Burn: Research Update, 2005, Web, Retrieved from: http://www.unm.edu/-lkravitz/Article%20folder/epocarticle.html.

Tanaka et al., "Age-predicted maximal heart rate revisited," Journal of the American College of Cardiology, vol. 37, Issue 1, pp. 153-156 (Jan. 2001).

Song et al., "Training Activity Recognition Systems Online Using Real-Time Crowdsourcing", University of Rochester Computer Science, UbiCom' 12, Sep. 5-8, 2012 (2 pages).

Sabatini, "Kalman-filter-based orientation determination using inertial/magnetic sensors: observability analysis and performance evaluation", Sep. 27, 2011, Sensors 2011, 11, 9182-9206.

Rowlands et al. "Assessing Sedentary Behavior with the GENEActiv: Introducing the Sedentary Sphere", Medicine and science in sports and exercise, 46.6 (2014), pp. 1235-1247.

Rapoport et al., "Metabolic Factors Limiting Performance in Marathon Runners" PLoS Computational Biology, vol. 6, Issue 10, 13 pages (Oct. 2010).

Noakes et al.. "Lore of Running," Fourth Edition, Human Kinetics, Chapter 2: Oxygen Transport, Chapter 3: Energy Systems, 157 pages (2002).

Myers et al., "Exercise Capacity and Mortality Among Men Referred for Exercise Testing," The New England Journal of Medicine, vol. 346, No. 11, pp. 793-801 (Mar. 14, 2002).

McArdle et al., "Exercise Physiology: Nutrition, Energy and Human Performance", Seventh Edition, Lippincott Williams & Wilkins, Chapter 5: Introduction to Energy Transfer, Chapter 6: Energy Transfer in the Body, Chapter 7: Energy Transfer in Exercise, Chapter 8: Measurement of Human Energy Expenditure, Chapter 9: Human Energy Expenditure During Rest and Physical Activity, Chapter 10: Energy Expenditure During Walking, Jogging, running and Swimming, Chapter 11: Individual Differences and Measurement of Energy Capacities, Chapter 21: Training for Anaerobic and Aerobic Power, 184 pages (2010).

Margaria et al., "Energy cost of running," Journal of Applied Physiology, vol. 18, No. 2, pp. 367-370 (Mar. 1, 1963).

Lucas et al, "Mechanisms of orthostatic intolerance following very prolonged exercise", 2008, J Appl Physiol, 105: 213-225.

(56) References Cited

OTHER PUBLICATIONS

Lavie et al., "Impact of cardiorespiratory fitness on the obesity paradox in patients with heart failure," Mayo Clinic Proceedings, vol. 88, No. 3, pp. 251-258 (Mar. 2013).
Kunze et al. "Where am I: Recognizing on-body positions of wearable sensors." Location-and context-awareness. Springer Berlin Heidelberg, 2005. 264-275.
KINprof, 2011, Predictive VO2max tests, Web Video, Retrieved from: https://www.youtube.com/watch?v=_9e3HcY1sm8.
Keytel et al, "Prediction of energy expenditure from heart rate monitoring during submaximal exercise", Journal of Sports Sciences, 23(3), 2005: 289-297.
Jackson et al., "Prediction of functional aerobic capacity without exercise testing, Medicine and Science in Sports and Exercise", 22(6), 863-870, 1990.
Isaacs et al., "Modeling energy expenditure and oxygen consumption in human exposure models: accounting for fatigue and EPOC", 2008, Journal of Exposure Science and Environmental Epidemiology, 18: 289-298.
Human Kinetics, Aerobic Workout Components, 2011, Web, Retrieved from: http://www.humankinetics.com/excerpts/excerpts/aerobicworkoutcomponentsexcerpt.
Hasson et al., "Accuracy of four resting metabolic rate production equations: Effects of sex, body mass index, age, and race/ethnicity", Journal of Science and Medicine in Sport, 2011, vol. 14, p. 344-351.
Glass et al., "ACSM's Metabolic Calculations Handbook," Lippincott Williams & Wilkins, 124 pages (2007).
Gao et al., "Evaluation of accelerometer based multi-sensor versus single-sensor activity recognition systems", Medical engineering & physics 36.6 (2014): 779-785.
Frankenfield et al., "Comparison of Predictive Equations for Resting Metabolic Rate in Healthy Nonobese and Obese adults: A systematic review. Journal of the American Dietetic Association", May 2005, vol. 105, No. 5, p. 775-789.
Fox et al., "Physical Activity and the Prevention of Coronary Heart Disease," Bull. N.Y. Acad. Med., vol. 44, No. 8, pp. 950-967 (Aug. 1968).
Earnest et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).
Chu, "In-Vehicle Driver Detection Using Mobile Phone Sensors", Submitted for Graduation with departmental Distinction in Electrical and Computer Engineering, Apr. 20, 2011, pp. 1-21.
Cavanagh et al., "The effect of stride length variation on oxygen uptake during distance running," Medicine and Science in Sports and Exercise, vol. 14, No. 1, pp. 30-35 (1982).
Burke et al., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).
Bruce et al., "Maximal oxygen intake and nomographic assessment of functional aerobic impairment in cardiovascular disease," American Heart Journal, vol. 85, Issue 4, pp. 546-562 (Apr. 1973).
Bruce et al., "Exercising testing in adult normal subjects and cardiac patients," Pediatrics, vol. 32, No. Suppl., pp. 742-756 (Oct. 1963).
Brooks et al., "Exercise Physiology: Human Bioenergetics and Its Applications," Fourth Edition, McGraw Hill. ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), 02 Deficit, 02 Debi, and the Anaerobic Threshold, Chapter 16: Cardiovascular Dynamics During Exercise, Chapter 2-1: Principles of Endurance Condifoning, hooter 27: Exercise Testing and Prescription 141 pages (2004).
Bo et al, "TEXIVE: Detecting Drivers Using Personal Smart Phones by Leveraging Inertial Sensors", Department of Computer Science, Illinois Institute of Technology, Chicago IL, Dec. 7, 2014, pp. 1-12.

"Your Fitness FAQ, Why is it important to warm up and cool down in a workout?", 2012, Web, Retrieved from: http://www.yourfitnessfaq.com/whyisitimportanttowarmupandcooldowninaworkout.html.
U.S. Appl. No. 15/692,726, Yet to Published, Aug. 31, 2017, Pending.
U.S. Appl. No. 15/692,237, Yet to Published, Aug. 31, 2017, Pending.
U.S. Appl. No. 15/692,736, Yet to Published, Aug. 31, 2017, Pending.
U.S. Appl. No. 15/691,245, Yet to Published, Aug. 30, 2017, Pending.
U.S. Appl. No. 15/689,113, Yet to Published, Aug. 29, 2017, Pending.
U.S. Appl. No. 15/679,538, Yet to Published, Aug. 17, 2017, Pending.
U.S. Appl. No. 15/678,645, Yet to Published, Aug. 16, 2017, Pending.
U.S. Appl. No. 15/616,135, Yet to Published, Jun. 7, 2017, Pending.
U.S. Appl. No. 15/611,010, Yet to Published, Jun. 1, 2017, Pending.
U.S. Appl. No. 15/466,397, Publication No. 2017-0273619, Mar. 22, 2017, Published.
U.S. Appl. No. 15/273,054, Publication No. 2017-0094450, Sep. 22, 2016, Published.
U.S. Appl. No. 15/273,038, Publication No. 2017-0082649, Sep. 22, 2016, Published.
U.S. Appl. No. 15/264,976, Publication No. 2017-0074897, Sep. 14, 2016, Published.
U.S. Appl. No. 14/501,930, Publication No. 2016-0058329, Sep. 30, 2014, Issued.
U.S. Appl. No. 14/502,827, Publication No. 2016-0058302, Sep. 30, 2014, Published.
U.S. Appl. No. 14/501,701, Publication No. 2016-0058332, Sep. 30, 2014, Published.
U.S. Appl. No. 14/502,809, Publication No. 2016-0058333, Sep. 30, 2014, Published.
U.S. Appl. No. 14/502,781, Publication No. 2016-0058372, Sep. 30, 2014, Published.
U.S. Appl. No. 14/502,754, Publication No. 2016-0058371, Sep. 30, 2014, Published.
U.S. Appl. No. 14/501,771, Publication No. 2016-0058370, Sep. 30, 2014, Published.
U.S. Appl. No. 14/493,178, Publication No. 2015-0087929, Sep. 22, 2014, Published.
U.S. Appl. No. 14/145,042, Publication No. 2015-0088006, Dec. 31, 2013, Published.
U.S. Appl. No. 14/501,634, Publication No. 2016-0058356, Sep. 30, 2014, Published.
U.S. Appl. No. 15/692,726, Publication No. 2018-0056123, Aug. 31, 2017, Published.
U.S. Appl. No. 15/692,237, Publication No. 2018-0056129, Aug. 31, 2017, Published.
U.S. Appl. No. 15/692,736, Publication No. 2018-0055375, Aug. 31, 2017, Published.
U.S. Appl. No. 15/689,113, Publication No. 2018-0055439, Aug. 29, 2017, Published.
U.S. Appl. No. 15/678,645, Publication No. 2018-0049694, Aug. 16, 2017, Published.
U.S. Appl. No. 15/616,135, Publication No. 2017-0347885, Jun. 7, 2017, Published.
U.S. Appl. No. 15/691,245, Publication No. 2018-0056128, Aug. 30, 2017, Published.
U.S. Appl. No. 15/679,538, Publication No. 2018-0050235, Aug. 17, 2017, Published.
U.S. Appl. No. 14/502,754, Publication No. 2016-0058371, Sep. 30, 2014, Issued.
U.S. Appl. No. 14/493,178, Publication No. 2015-0087929, Sep. 22, 2014, Abandoned.
U.S. Appl. No. 14/145,042, Publication No. 2015-0088006, Dec. 31, 2013, Abondoned.
International Search Report and Written Opinion received for PCT Application No. PCT/US2017/049693, dated Dec. 8, 2017, 9 pages.
Novatel, "IMU Error and Their Effects", Novatel Application Notes APN-064 Rev A p. 1-6, Feb. 21, 2014.

(56) References Cited

OTHER PUBLICATIONS

International Search Report and Written Opinion received for PCT Patent Application No. PCT/US2018/047290, dated Nov. 8, 2018, 14 pages.

* cited by examiner

STATISTICAL HEART RATE MONITORING FOR ESTIMATING CALORIE EXPENDITURE

CROSS-REFERENCE TO RELATED APPLICATIONS

This application claims priority to U.S. Provisional Application No. 62/129,510, filed Mar. 6, 2015, entitled "Statistical Heart Rate Monitoring for Estimating Calorie Expenditure," which is hereby incorporated by reference in its entirety. This application is related to U.S. patent application Ser. No. 14/501,634, titled "Method and System to Calibrate Fitness Level and Direct Calorie Burn Using Motion, Location Sensing, and Heart Rate," filed Sep. 30, 2014, which is hereby incorporated by reference in its entirety.

FIELD

The present disclosure relates generally to improving calorie expenditure prediction and tracking and, more particularly, to techniques for statistical heart rate monitoring and calorimetry using data from motions sensors and heart rate sensors.

BACKGROUND

An individual's health or fitness can be assessed from the perspective of energy expenditure over time. One technique for estimating energy expenditure, or calorie burn, is based on heart rate. During moderate to vigorous exercise, heart rate is correlated with energy expenditure.

At a macroscopic level, an individual's heart rate indicates how quickly the individual's body is delivering oxygen to vital organs and tissues, which consume the oxygen through oxidative cellular metabolism. The heart pumps blood through the lungs, where blood cells absorb oxygen from the lungs. This oxygen-rich blood returns to the heart, from which it is pumped through blood vessels that distribute the blood throughout the body to its organs and tissues. Tissues absorb oxygen carried by the blood and use the oxygen in chemical reactions of oxidative metabolism, also known as aerobic metabolism, to provide energy for biological functions.

The rate at which an individual body consumes oxygen at a given point in time is referred to as the volumetric flow of oxygen into the tissues of the body, also known as "oxygen exchange rate," "oxygen uptake rate," or simply $\dot{V}O_2$ (e.g., liters of oxygen per minute). Controlling for differences in body size, $\dot{V}O_2$ is often reported for a given individual in terms of oxygen volume at standard temperature and pressure per unit of time per unit of body mass (e.g., ml/kg/min).

Specifically, $\dot{V}O_2$ measures the overall rate at which the body is engaged in oxidative metabolism. $\dot{V}O_2$ during various physical activities—and, consequently, energy expenditure during those physical activities—varies from individual to individual. In a laboratory setting, it may be possible to use indirect calorimetry (e.g., with a $\dot{V}O_2$ mask, heart rate monitors, etc.), to measure an individual's aerobic capacity, also known as maximum $\dot{V}O_2$, or simply "$\dot{V}O_2$max." $\dot{V}O_2$max is the highest rate of oxygen exchange (e.g., measured with indirect calorimetry) that an individual can attain.

In addition to $\dot{V}O_2$max, several other parameters may be used to estimate an individual's energy expenditure at a given heart rate. Maximum heart rate ($HR_{max}$) is one example. An individual's heart rate generally will not exceed a maximum value, and, during exercise, the individual will reach this heart rate at their maximum energy output.

"Resting heart rate" (RHR) is another parameter. When at rest, an individual's heart rate will reach a minimum value. This parameter is sometimes also referred to as "basal heart rate" or "minimum heart rate".

When these parameters are known, it may be possible to calibrate a fitness tracking device with more accurate calorimetry. Thus, at a given heart rate during moderate to vigorous aerobic exercise, a device may be capable of calculating a calorie burn rate that is calibrated for the individual. However, in practice, many individuals will not know their maximum oxygen exchange rate ($\dot{V}O_2$max) or other parameters that may be used to calculate energy expenditure.

SUMMARY

Embodiments of the present disclosure include a fitness tracking device and techniques for accurately tracking an individual's energy expenditure over time and over a variety of activities while wearing the fitness tracking device. In some embodiments, the fitness tracking device may be a wearable device. The wearable device may be worn on a wrist, such as a watch, and it may include one or more microprocessors, a display, and a variety of sensors, including a heart rate sensor and one or more motion sensors.

Embodiments of the present disclosure may provide accurate, individualized calorimetry throughout a person's day, and across a variety of activities. Some embodiments may calibrate a fitness tracking device for an individual without necessarily relying on measuring $\dot{V}O_2$, heart rate testing, or self-reporting about physical activity.

In some embodiments, the heart rate sensor may include a photoplethysmogram (PPG) sensor for sensing heart rate. The PPG sensor can illuminate the user's skin using a light, such as a light-emitting diode (LED), and can measure changes in light absorption as blood is pumped through the subcutaneous tissue under the PPG sensor. The fitness tracking device can measure an individual's current heart rate from the PPG. The heart rate sensor may also be configured to determine a confidence level indicating a relative likelihood of an accuracy of a given heart rate measurement. The heart rate sensor may be configured to operate in any of several modes that may include a high-power mode and low-power mode, and the heart rate sensor may be off to conserve power and turned on in a periodic or on-demand manner.

In some embodiments, the motion sensors may include, for example, an accelerometer, a gyroscope, a barometer or altimeter, a magnetometer or compass, etc. The fitness tracking device may also include a motion coprocessor, which may be optimized for low-power, continuous motion sensing and processing.

In some embodiments, the fitness tracking device may be capable of communicating with a companion device. The fitness tracking device may communicate with a companion device wirelessly, e.g., via a Bluetooth connection or similar wireless communication method. The companion device may be a second mobile device, such as a phone, which may include additional sensors. The additional sensors in the companion device may include a Global Positioning System (GPS) sensor, accelerometer, gyroscope, barometer or altimeter, motion coprocessor, etc. The companion device may, for example, communicate location information based on data from the GPS sensor to the fitness tracking device.

In some embodiments, a new fitness tracking device may be calibrated to measure energy expenditure based on heart rate and motion data. Out of the box, the new fitness tracking device may assume default values for a set of parameters of the user (e.g., $\dot{V}O_2$max, $HR_{max}$, and RHR), which in turn may be used to estimate calorie burn for a variety of activities. As the user wears the new fitness tracking device over time, the new fitness tracking device may improve its estimate or calibration of the user's parameters.

In some embodiments, a fitness tracking device may apply particular models and algorithms based on prior calibration to compute energy expenditure given information about the user's heart rate, or motion, or a combination of the two.

In some embodiments, systems and methods are disclosed for improving a fitness tracking device such that the fitness tracking device tracks physiological states and parameters for calorie estimation. In some embodiments, the systems and methods include determining, by a wearable computing device, a start of an exercise session associated with a user of the wearable computing device, the wearable computing device including a processor, a heart rate sensor, and at least one of a motion sensing module, a display module, and an interface module. In some embodiments, the systems and methods include measuring, by the heart rate sensor of the wearable computing device, heart rate data for a first period of time, the first period of time associated with the start of the exercise session. In some embodiments, the systems and methods include determining, by the processor of the wearable computing device, an onset heart rate value of the user based on the measured heart rate data, the onset heart rate value associated with a lowest valid heart rate measured during the first period of time. In some embodiments, the systems and methods include associating, by the processor of the wearable computing device, a resting heart rate parameter (RHR) of a calorimetry model to at least one of the onset heart rate value, a preset RHR, and an RHR based on user biometric data. In some embodiments, the systems and methods include estimating, by the processor of the wearable computing device, energy expenditure of the user during a second period of time based on the calorimetry model and a plurality of heart rate measurements (HR) obtained by the wearable computing device during the second period of time, the second period of time associated with a portion of time after the first period of time and prior to an end of the exercise session.

In some embodiments, estimating the energy expenditure further comprises calculating a fraction of heart rate reserve (FHR), wherein $FHR=(HR_{max}-HR)/(HR_{max}-RHR)$. In some embodiments, the energy expenditure is proportional to a function $f(FHR)$, wherein $f(FHR)$ is approximately a sigmoidal nonlinearity. In some embodiments, $f(0)=1$ and $f(1)=0$. In some embodiments, $HR_{max}$ is based on at least one of an age of the user, and at least one of a previously measured heart rate. In some embodiments, $\dot{V}O_2$max comprises one of a default value or a value previously calibrated by the user. In some embodiments, the at least one of a previously measured heart rate comprises at least one of a maximum heart rate value of the at least one of a previously measured heart rate; a percentile of the at least one of a previously measured heart rate; a percentile of the at least one of a previously measured heart rate above a first threshold heart rate value; a percentile of the at least one of a previously measured heart rate above a $HR_{max}$ based on the age of the user; and a maximum heart rate value being less than a percentage of the $HR_{max}$ based on the age of the user. In some embodiments, the percentile of the at least one of a previously measured heart rate is approximately a $98^{th}$ percentile. In some embodiments, the percentile of the at least one of a previously measured heart rate above a first threshold heart rate value is approximately a $98^{th}$ percentile, the percentile of the at least one of a previously measured heart rate above a $HR_{max}$ based on the age of the user is approximately a $98^{th}$ percentile; and the percentage of the $HR_{max}$ based on the age of the user is approximately 110%. In some embodiments, the preset RHR comprises at least one of a minimum value of a list of RHR values from prior exercise sessions; a percentile of the list of RHR values from prior exercise sessions; and a percentile of RHR values in the list below a second threshold heart rate value. In some embodiments, the second threshold heart rate value comprises 90 beats per minute. In some embodiments, the RHR is further associated with the lower of the preset value; and the RHR based on user biometric data. In some embodiments, the preset value comprises 72 beats per minute; and the RHR based on user biometric data comprises a heart rate value based on a maximum oxygen exchange rate of the user ($\dot{V}O_2$max) and a maximum heart rate of the user ($HR_{max}$). In some embodiments, the first period of time comprises 10 seconds to 1 minute. In some embodiments, the first period of time is associated with a timer, wherein the timer activates at least one of a low-power mode of heart rate sensing and a high-power mode of heart rate sensing.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

DESCRIPTION

There is growing interest to assess and monitor one's health or fitness and physical activity. The present disclosure describes a fitness tracking device that may be configured to provide an accurate, individualized quantification of energy expenditure over time and across a variety of activities. The device may implement sophisticated calorimetry techniques based on empirical models and sophisticated algorithms that may use motion data, heart rate data, or a weighted combination of both motion data and heart rate data.

Figure 1:
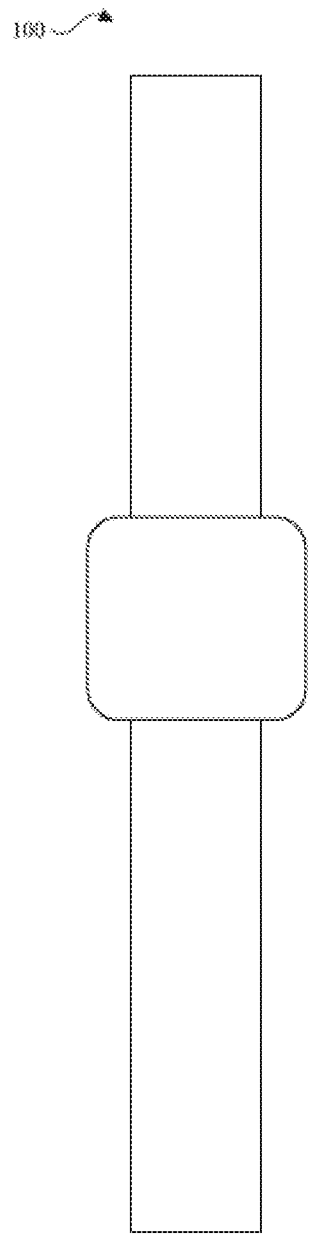
FIG. 1 shows a fitness tracking device in accordance with an embodiment of the present disclosure.

FIG. 1 shows an example of a fitness tracking device 100 in accordance with an embodiment of the present disclosure. In some embodiments, the fitness tracking device 100 may be a wearable computing device, such as a watch configured to be worn around an individual's wrist. As described in more detail below, the fitness tracking device 100 may be calibrated according to physical attributes of the individual and physical activity by the individual user who is wearing the fitness tracking device 100, including, for example, heart rate statistics.

Figure 2:
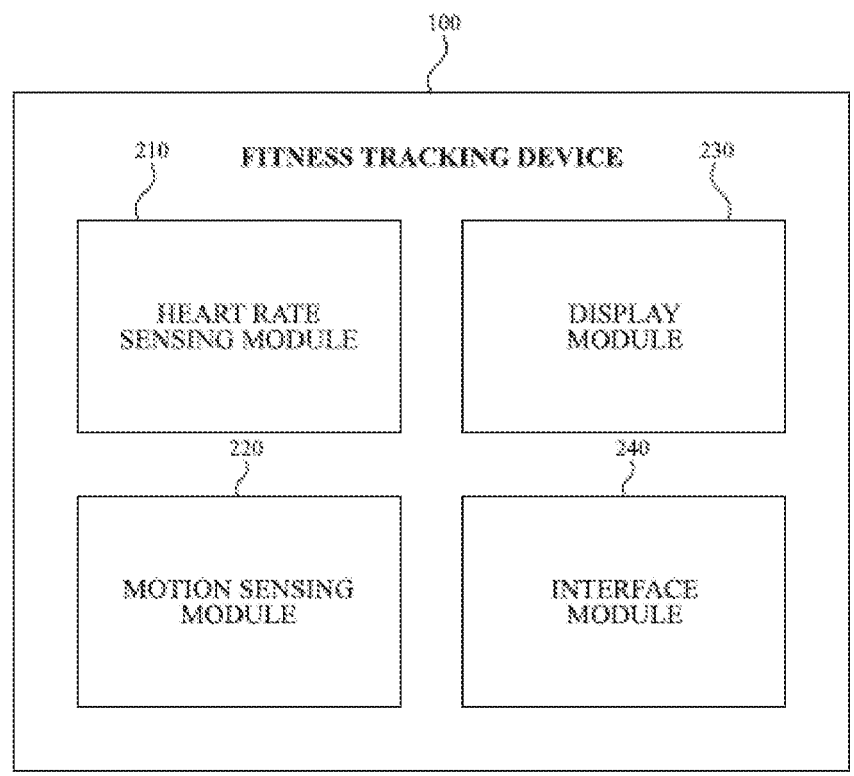
FIG. 2 depicts a block diagram of a fitness tracking device in accordance with an embodiment of the present disclosure.

FIG. 2 depicts a block diagram of example components that may be found within the fitness tracking device 100 in accordance with an embodiment of the present disclosure. These components may include a heart rate sensing module 210, a motion sensing module 220, a display module 230, and an interface module 240.

The heart rate sensing module 210 may include or may be in communication with a photoplethysmogram "PPG" sensor as previously described. The fitness tracking device 100 can measure an individual's current heart rate from the PPG. The heart rate sensor may also be configured to determine a confidence level indicating a relative likelihood of an accuracy of a given heart rate measurement. In other embodiments, a traditional heart rate monitor may be used and may communicate with the fitness tracking device 100 through a near field communication method (e.g., Bluetooth).

The fitness tracking device 100 may include an LED and a photodiode or the equivalent to obtain a PPG. The fitness tracking device 100 may subsequently determine the user's current heart rate based on the PPG data.

To conserve battery power on the fitness tracking device 100, the LED may be a relatively low-power LED, such as a green LED. In some embodiments, to further conserve power on the fitness tracking device 100, the fitness tracking device 100 may be configured to check heart rate at periodic intervals (e.g., once per minute, or once per three minutes). The period for checking heart rate may change dynamically. For example, if the fitness tracking device 100 automatically detects or receives input from the user that the user is engaged in a certain level, intensity, or type of physical activity (e.g., "in session"), the fitness tracking device may check heart rate more frequently (e.g., once per thirty seconds, once per minute, etc.). The fitness tracking device 100 may use, for example, machine learning techniques, battery power monitoring, or physical activity monitoring to balance the frequency of heart rate samples for accurate calorimetry with power optimization.

In addition to the heart rate sensing module 210, the fitness tracking device 100 may also include the motion sensing module 220. The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the fitness tracking device 100 may receive motion information from the motion sensors of the motion sensing module 220 to track acceleration, rotation, position, or orientation information of the fitness tracking device 100 in six degrees of freedom through three-dimensional space.

In some embodiments, the motion sensing module 220 may include other types of sensors in addition to accelerometers and gyroscopes. For example, the motion sensing module 220 may include an altimeter or barometer, or other types of location sensors, such as a GPS sensor.

In some embodiments, the fitness tracking device 100 may take advantage of the knowledge that the heart rate sensing module 210 and the motion sensing module 220 are approximately collocated in space and time to combine data from each module 210 and 220 to improve the accuracy of its calorimetry functionality. Depending on the current activity and a determination of a confidence of current heart rate and motion data, the fitness tracking device 100 may also rely on one of either the heart rate or a motion-derived work rate to estimate energy expenditure more accurately.

The fitness tracking device 100 may also include a display module 230. Display module 230 may be a screen, such as a crystalline (e.g., sapphire) or glass touchscreen, configured to provide output to the user as well as receive input form the user via touch. For example, display 230 may be configured to display a current heart rate or a daily average energy expenditure. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the fitness tracking device 100 may present output to the user in other ways, such as by producing sound with a speaker (not shown), and the fitness tracking device 100 may receive input from the user in other ways, such as by receiving voice commands via a microphone (not shown).

In some embodiments, the fitness tracking device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The fitness tracking device 100 may be configured to communicate with a companion device 300 (FIG. 3), such as a smartphone, as described in more detail herein. In some embodiments, the fitness tracking device 100 may be configured to communicate with other external devices, such as a notebook or desktop computer, tablet, headphones, Bluetooth headset, etc.

The modules described above are examples, and embodiments of the fitness tracking device 100 may include other modules not shown. For example, the fitness tracking device 100 may include one or more microprocessors (not shown) for processing heart rate data, motion data, other information in the fitness tracking device 100, or executing instructions for firmware or apps stored in a non-transitory processor-readable medium such as a memory module (not shown). Additionally, some embodiments of the fitness tracking device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
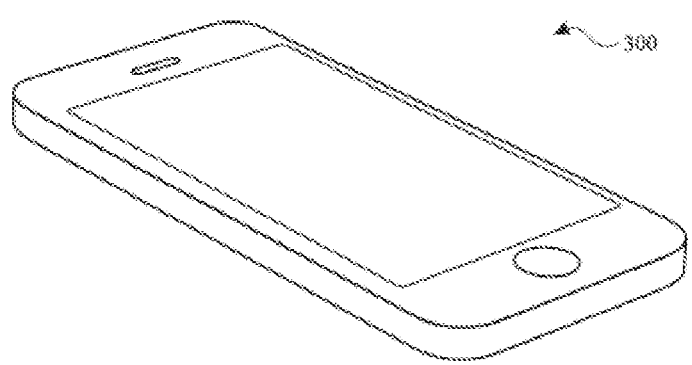
FIG. 3 shows a companion device in accordance with an embodiment of the present disclosure.

FIG. 3 shows an example of a companion device 300 in accordance with an embodiment of the present disclosure. The fitness tracking device 100 may be configured to communicate with the companion device 300 via a wired or wireless communication channel (e.g., Bluetooth, Wi-Fi, etc.). In some embodiments, the companion device 300 may be a smartphone, tablet, or similar portable computing device. The companion device 300 may be carried by the user, stored in the user's pocket, strapped to the user's arm with an armband or similar device, placed on a table, or otherwise positioned within communicable range of the fitness tracking device 100.

The companion device 300 may include a variety of sensors, such as location and motion sensors (not shown). When the companion device 300 may be optionally available for communication with the fitness tracking device 100, the fitness tracking device 100 may receive additional data from the companion device 300 to improve or supplement its calibration or calorimetry processes. For example, in some embodiments, the fitness tracking device 100 may not include a GPS sensor as opposed to an alternative embodiment in which the fitness tracking device 100 may include a GPS sensor. In the case where the fitness tracking device 100 may not include a GPS sensor, a GPS sensor of the companion device 300 may collect GPS location information, and the fitness tracking device 100 may receive the GPS location information via interface module 240 (FIG. 2) from the companion device 300.

In another example, the fitness tracking device 100 may not include an altimeter, as opposed to an alternative embodiment in which the fitness tracking device 100 may include an altimeter. In the case where the fitness tracking device 100 may not include an altimeter or barometer, an altimeter or barometer of the companion device 300 may collect altitude or relative altitude information, and the fitness tracking device 100 may receive the altitude or relative altitude information via interface module 240 (FIG. 2) from the companion device 300.

For example, and as explained above, an individual exhibits a correlation between heart rate (varying between the individual's resting heart rate RHR and maximum heart rate $HR_{max}$) and $\dot{V}O_2$ (up to the individual's aerobic capacity, or $\dot{V}O_2max$). Thus, there is also a correlation between heart rate and energy expenditure. Additionally, $\dot{V}O_2$ is linked to a user's aerobic power output based on the user's metabolic rate, which may also vary from one individual to the next. Metabolic rate may be expressed in Metabolic Equivalents of Task, or METs. METs indicates how many calories a "typical" individual burns per unit of body mass per unit of time. An individual's RHR is also referred to herein as a minimum heart rate $HR_n$. Resting heart rate is the heart rate obtained in a specific resting protocol, while the minimum heart rate is the minimum heart rate observed. Except for disease states (such as abnormal heart rhythms), these can safely assumed to be equal.

If the user's weight is known, and the user undergoes testing to measure the user's maximum heart rate and $\dot{V}O_2max$, a device may be able to construct an individualized model of energy expenditure for a given heart rate.

In situations such as laboratory testing, it may be possible to test and measure a user's $\dot{V}O_2max$ and maximum heart rate ("$HR_{max}$"). With these predetermined values, a device may be able to estimate energy expenditure more accurately based on a user's current heart rate during moderate to high-intensity physical activity or exercise. Without laboratory testing (e.g., testing based on indirect calorimetry), $\dot{V}O_2max$ and $HR_{max}$ may be estimated with other methods, such as submaximal exercise testing or non-exercise testing. For example, $HR_{max}$ may be estimated based on the user's age. In some embodiments, if a heart rate greater than $HR_{max}$ is observed, then the device may update the estimate of $HR_{max}$ to use the higher, observed heart rate. In some embodiments, the device may determine whether to use an age-based estimate or a higher observed heart rate based on a confidence level for the heart rate measurement or whether the higher observed heart rate was sustained for a threshold period of time.

An individual's current heart rate (HR) as it compares to the range of an individual's heart rate from resting heart rate RHR (e.g., $HR_{min}$ or $HR_{onset}$) and maximum heart rate $HR_{max}$ may be expressed as a value called "Fraction of Heart Rate Reserve" (FHR):

$$FHR=(HR_{max}-HR)/(HR_{max}-RHR) \quad (Eq. 1)$$

FHR may range from 0 to 1 for any individual. When an individual's FHR is close to 0, it indicates that the user's heart rate HR is close to the individual's maximum heart rate. Similarly, when an individual's FHR is close to 1, it indicates that the individual's heart rate is close to the individual's resting heart rate (e.g., $HR_{min}$ or $HR_{onset}$). Thus, for example, if the individual's FHR is less than 0.5, the user's heart rate is closer to maximum heart rate than to resting heart rate.

Energy expenditure (EE) may be determined using a calorimetry model with a parameterized function of FHR:

$$EE=\dot{V}O_2max \cdot f(FHR) \quad (Eq. 2)$$

The function $f(FHR)$ may be an approximately sigmoidal nonlinearity. When FHR=0, $f(0)$ may equal 1. $f(1)$ may equal 0, or a fractional margin above 0 (e.g., approximately 0.1, 0.2, or 0.3). The slope of the function $f(FHR)$ may be approximately 1 (i.e., the "unity" slope) for a range of FHR, such as when FHR=[0, 0.5], or FHR=[0, 0.6]. In other embodiments, other definitions are associated with $f(FHR)$, including other minimum and maximum values, or other slopes, including other regions or ranges of FHR for which the function's slope equals 1 or approximately 1.

The user's resting heart rate (RHR), which, in some embodiments, may be represented as the user's minimum heart rate ($HR_{min}$ or $HR_0$) may be observed by the device as well or adjusted if even lower measurements are observed. In some embodiments, RHR may be represented by the user's heart rate at the onset of an exercise session ($HR_{onset}$), which may be higher than the users $HR_{min}$ under certain circumstances, such as when the user has recently finished a prior exercise session. In some instances, as described in greater detail below, the calorimetry model may be more accurate when $HR_{onset}$ is used as the value of the RHR parameter instead of $HR_{min}$.

Figure 4:
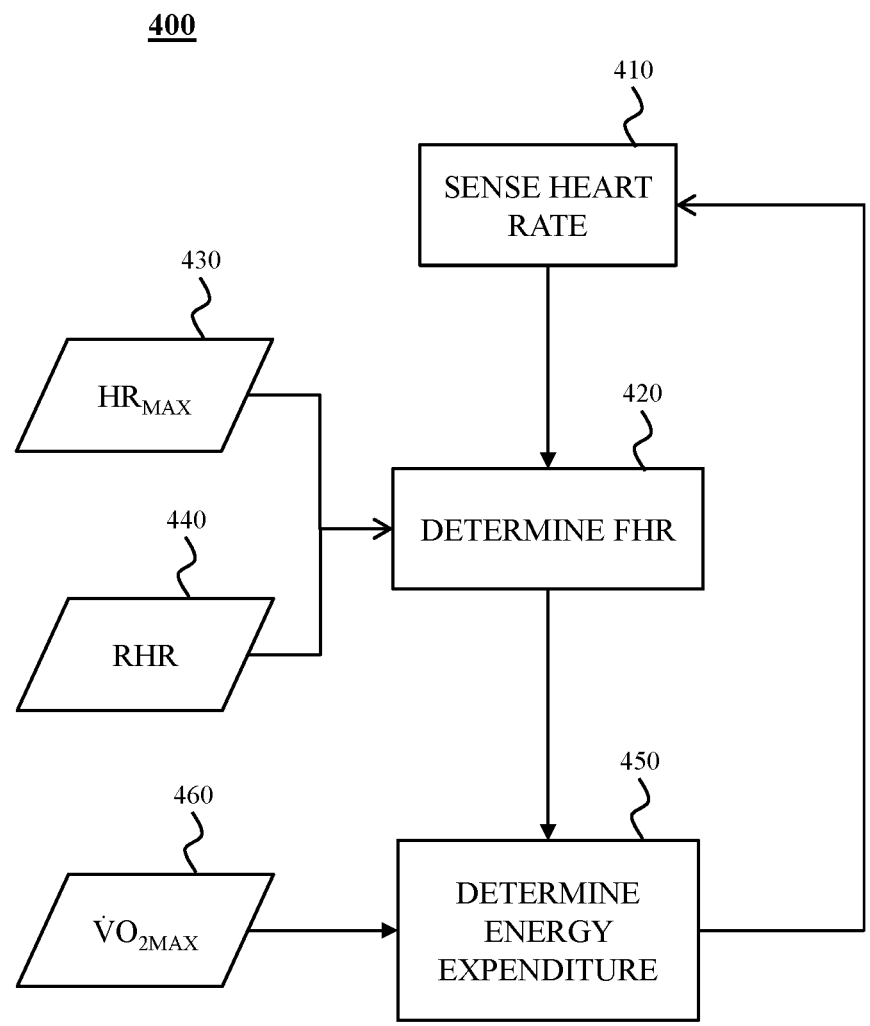
FIG. 4 shows a calorimetry method in accordance with an embodiment of the present disclosure.

FIG. 4 shows a calorimetry method 400 using $\dot{V}O_2max$ and heart rate, in accordance with an embodiment of the present disclosure. Calorimetry method 400 may begin at block 410.

At block 410, the user's current heart rate (HR) may be sensed. In some embodiments, the user's heart rate may be sensed using the heart rate sensing module 210 of the fitness tracking device 100. The user's heart rate may be provided as input to block 420.

At block 420, the user's current Fraction of Heart Rate Reserve (FHR) may be determined. In some embodiments, the user's current FHR may be determined according to Eq. 1, which is a function of heart rate (HR), parameterized by $HR_{max}$ and RHR. In some embodiments, the value of the $HR_{max}$ parameter may be provided by $HR_{max}$ input 430, and the value of the RHR parameter may be provided by RHR input 440. Inputs 430 and 440 may be retrieved from a memory of the fitness tracking device 100. Inputs 430 and 440 may be represented by default values or values that were previously calibrated for the user using various techniques described herein. In some embodiments, one or more of inputs 430 and 440 may be measured, calibrated, or otherwise determined during the execution of calorimetry method 400. The user's FHR may be provided as input to block 450.

At block 450, the user's current rate of energy expenditure may be determined. In some embodiments, the user's current rate of energy expenditure may be determined by a calorimetry model according to Eq. 2, which is a function of FHR, parameterized by $\dot{V}O_2$max. In some embodiments, the value of the $\dot{V}O_2$max parameter may be provided by $\dot{V}O_2$max input 460. Input 460 may be represented by a default value or a value that was previously calibrated for the user. The determined rate of energy expenditure may be stored in a memory of the fitness tracking device 100, output to another process, or otherwise aggregated within calorimetry method 400.

In some embodiments, calorimetry method 400 may return to block 410, repeating the determination of energy expenditure for the user's current heart rate at subsequent points in time until the user or another process of the fitness tracking device 100 halts or pauses calorimetry method 400.

Figure 5:
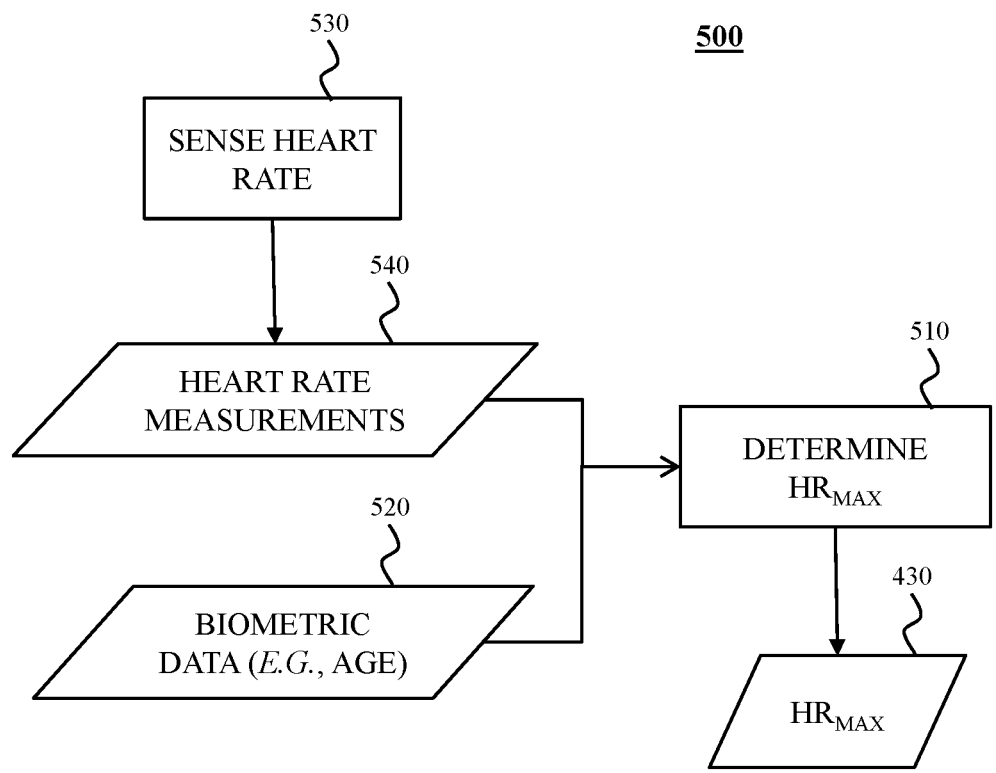
FIG. 5 depicts a calibration method for determining a value for the $HR_{max}$ parameter in accordance with an embodiment of the present disclosure.

FIG. 5 depicts a calibration method 500 for determining a value for the $HR_{max}$ parameter in accordance with an embodiment of the present disclosure. The calibration method 500 may begin at block 510.

At block 510, a value for the user's $HR_{max}$ may be determined. In some embodiments, the user's $HR_{max}$ may be determined according to the following equation (Eq. 3):

$$HR_{max}=A-B(\text{age}) \quad (\text{Eq. 3})$$

Eq. 3 describes the inverse relationship between a user's maximum heart rate $HR_{max}$ and the user's age—as the user gets older, the user's maximum heart rate decreases. Calibration method 500 may select values for constants A and B in Eq. 3 to estimate the user's $HR_{max}$. For example, A may equal 200, or 205, or 210, etc., and B may equal 0.9, 0.8, 0.7, etc.

Block 510 may receive biometric data about the user at input 520. In some embodiments, biometric data may include the user's age. In some embodiments, the fitness tracking device 100 may determine the user's age based on the user's birthday or birth year in comparison to a current date or year. As time passes and the user ages, the fitness tracking device 100 may automatically increase the age value at input 520 and may automatically determine a new $HR_{max}$ for the user.

In some embodiments, the user's $HR_{max}$ may be determined using previously measured heart rate measurements 540. The previously measured heart rate measurements may have been previously sensed at 530 using the heart rate sensing module 210 of the fitness tracking device 100.

The heart rate measurements 540 may be used in a variety of techniques to predict or help predict the user's $HR_{max}$. For example, in some embodiments, the fitness tracking device 100 may compile a list of heart rate measurements 540 and apply a statistical function (or "statistical estimator") to select, compute, or otherwise determine a value to use as $HR_{max}$. For example, block 510 (or another process of the fitness tracking device 100) may select the maximum value from the heart rate measurements to use as $HR_{max}$.

Another example of a statistical estimator for $HR_{max}$ may be to determine a percentile (e.g., the 95th percentile, or the 98th percentile), of all of the heart rate measurements.

Yet another statistical estimator for $HR_{max}$ may be to determine a percentile (e.g., the 95th percentile, or the 98th percentile), of all of the heart rate measurements that were above a cutoff value (e.g., 100 beats per minute, or 150 beats per minute, etc.), if any.

Yet another statistical estimator for $HR_{max}$ may be to determine a percentile (e.g., the 95th percentile, or the 98th percentile), of all of the heart rate measurements that were above a threshold fraction of the user's $HR_{max}$ as determined based on the user's age (e.g., measurements above 85% of the age-based $HR_{max}$, or above 90% of the age-based $HR_{max}$, etc.), if any. In some embodiments, this statistical estimator may establish a lower bound on observed $HR_{max}$ using the age-based $HR_{max}$.

Yet another statistical estimator for $HR_{max}$ may be to determine a percentile (e.g., the 95th percentile, or the 98th percentile), of all of the heart rate measurements that were below a threshold fraction of the user's $HR_{max}$ as determined based on the user's age (e.g., measurements below 110% of the age-based $HR_{max}$, or below 115% of the age-based $HR_{max}$, etc.), if any. In some embodiments, this statistical estimator may establish an upper bound on observed $HR_{max}$ using the age-based $HR_{max}$.

Yet another statistical estimator for $HR_{max}$ may take into account both a lower bound and an upper bound on observed $HR_{max}$ using the age-based $HR_{max}$, such as using the lower-bound and upper-bound techniques described above.

In some embodiments, block 510 may determine $HR_{max}$ using either the user's biometric data at input 520 or the user's heart rate measurements at input 540, or a combination of both inputs 520 and 540. The value of $HR_{max}$ determined at block 510 may be stored, transmitted, or otherwise used as the $HR_{max}$ parameter 430 in calorimetry method 400.

Figure 6:
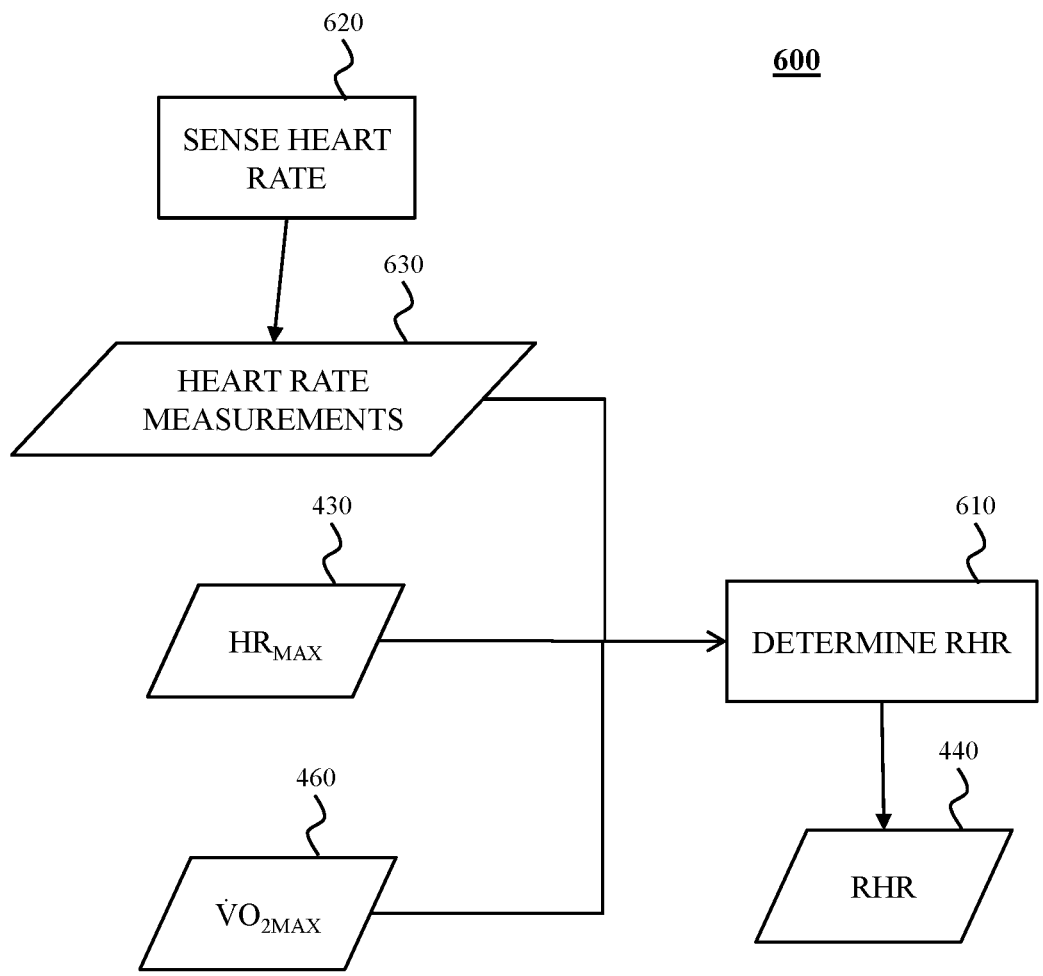
FIG. 6 shows a calibration method for determining a value for the RHR parameter in accordance with an embodiment of the present disclosure.

FIG. 6 shows a calibration method 600 for determining a value for the RHR parameter in accordance with an embodiment of the present disclosure. The calibration method 600 may begin at block 610.

At block 610, a value for the user's RHR may be determined. In some embodiments, RHR may be set to a default value (e.g., 70 beats per minute, 72 beats per minute, 75 beats per minute, etc.)

In some embodiments, the user's RHR may be determined according to the following equation (Eq. 4):

$$RHR=A \cdot HR_{max}/\dot{V}O_2\text{max} \quad (\text{Eq. 4})$$

Eq. 4 describes the relationship between a user's resting heart rate (RHR) and some of the user's other biometrics, i.e., the user's maximum heart rate ($HR_{max}$) and the user's maximum rate of oxygen exchange ($\dot{V}O_2$max). Eq. 4 predicts that a user with a relatively low ratio of $HR_{max}$ to $\dot{V}O_2$max may have a relatively lower RHR as well. Eq. 4 includes a scaling parameter (A) to convert the ratio of $HR_{max}$ to $\dot{V}O_2$max into an estimate of RHR in beats per minute. The scaling parameter in Eq. 4 (A) may be fixed or otherwise determined. In some embodiments, the scaling parameter (A) may equal, for example, approximately 10, 15, 20, etc.

In some embodiments, $HR_{max}$ parameter 430 and $\dot{V}O_2$max parameter 460 may be provided as inputs to block 610 so that RHR may be determined based on these values using, for example, the technique based on Eq. 4.

In some embodiments, the user's RHR may be determined using heart rate measurements 630. The heart rate measurements may have been previously sensed at 620 using the heart rate sensing module 210 of fitness tracking device 100. In some embodiments, the heart rate measurements 630 to determine RHR may include the heart rate measurements 540 used to determine $HR_{max}$. In other embodiments, some or all of the heart rate measurements 630 for RHR may have been collected separately from the heart rate measurements 540 for $HR_{max}$.

In some embodiments, RHR may be determined to be the lowest value determined by any of the previously described methods such as the default value (e.g., 70 beats per minute), the value based on the user's biometrics, or one or more of the values determined using heart rate measurements. In some embodiments, the lowest value includes the lowest valid heart rate measurement, where valid measurements may be determined by requiring a minimum signal to noise ratio on the underlying HR measurements, and/or an absolute or age-adjusted ranges for realistic HR values (e.g. valid HRs>30 bpm and <220 bpm). The value of RHR determined at block 610 may be stored, transmitted, or otherwise used as the RHR parameter 440 in calorimetry method 400.

The heart rate measurements 630 may be used in a variety of techniques to predict or help predict the user's RHR. For example, in some embodiments, the fitness tracking device 100 may compile a list of heart rate measurements 630 and apply a statistical estimator to select, compute, or otherwise determine a value to use as RHR. For example, block 610 (or another process of the fitness tracking device 100) may select the minimum value from the heart rate measurements to use as RHR. This minimum value may also be referred to as the user's minimum heart rate, $HR_{min}$.

Another example of a statistical estimator for RHR may be to determine a percentile (e.g., the 95th percentile, or the 98th percentile), of all of the heart rate measurements.

Yet another statistical estimator for RHR may be to determine a percentile (e.g., the 95th percentile, or the 98th percentile), of all of the heart rate measurements that were above a cutoff value (e.g., 60 beats per minute, or 70 beats per minute, etc.), if any.

Yet another statistical estimator for RHR may be to determine a percentile (e.g., the 95th percentile, or the 98th percentile), of all of the heart rate measurements that were above a cutoff value (e.g., 60 beats per minute, or 70 beats per minute, etc.), if any.

Yet another statistical estimator for RHR may be to determine a percentile (e.g., the 95th percentile, or the 98th percentile), of all of the heart rate measurements that were below a cutoff value (e.g., 100 beats per minute, or 90 beats per minute, etc.), if any.

Yet another statistical estimator for RHR may take into account both a lower bound and an upper bound on $HR_{onset}$, such as by using a combination of the lower-bound and upper-bound techniques described above.

The choice of which RHR value to use may depend on the specific activity selected, characteristics of the user, or characteristics of the HR measurement. For example, an RHR value to can be chosen for a given activity based on a) whether the user has exercised in the immediate vicinity of starting an activity, b) whether the HR readings at the start of the activity are reliable, c) which activity is being performed (e.g., elliptical vs. indoor cycling) and d) an estimate of the user's underlying fitness.

In some embodiments, the fitness tracking device 100 may enable collection (e.g., sensing) of heart rate measurements during a first portion of an exercise session. For example, when a user indicates that the user is starting an exercise session (e.g., via an interactive application running on the fitness tracking device 100), or when the fitness tracking device 100 detects the beginning of an exercise session (e.g., based on heart rate dynamics or motion data), the fitness tracking device 100 may record or otherwise add subsequent heart rate measurements to the heart rate measurements 630 for a period of time (e.g., for 10 seconds, 20 seconds, 30 seconds, one minute, etc.). Block 610 (or another process) may select the minimum value from—or apply a different statistical estimator to—this set of heart rate measurements to use at RHR. For these embodiments, the minimum value may also be referred to the heart rate at the onset of exercise ($HR_{onset}$).

In some situations, a user's $HR_{onset}$, measured around the time of the beginning of an exercise session, may be higher than the user's $HR_{min}$. For example, if the user had recently exercised earlier in the day, the user's heart rate may not have returned to the user's minimum (resting) heart rate (during a "cool down" period). Instead, $HR_{onset}$ may account for a higher heart rate at the beginning of an exercise session.

In some embodiments, $HR_{onset}$ may be computed during a period of time before the beginning of an exercise session. For example, the fitness tracking device 100 may determine that a user is about to begin an exercise session when the user opens a fitness tracking application. The fitness tracking device 100 may sense or otherwise collect heart rate measurements 630 for a period of time between the user activating the application and subsequently indicating within the application that the user is beginning an exercise session. In some embodiments, some of the heart rate measurements 630 may be collected prior to beginning an exercise session, and some of the heart rate measurements 630 may be collected after beginning the exercise session.

In some embodiments, $HR_{onset}$ may be determined by, for example, selecting the minimum value, or by computing the second percentile, of heart rate measurements collected prior to an exercise session (e.g., 5 minutes, 10 minutes, 15 minutes, 30 minutes, one hour, etc. prior to beginning an exercise session).

In some embodiments, $HR_{onset}$ may be determined by, for example, selecting the minimum value, or by computing a percentile, of heart rate measurements collected for a period of time (e.g., 30 minutes, 60 minutes, etc.) ending before the exercise session begins (e.g., ending 10 minutes, 15 minutes, etc. before the exercise session begins).

In some embodiments, $HR_{onset}$ may be determined using weighted sums of heart rate measurements from a period of time, such as a period of time 45 minutes or 60 minutes before the exercise session begins. For example, the weights may be based on the value of the heart rate measurement relative to a fixed value, or relative to other heart rate measurements collected during this period of time. For another example, the weights may be based on the time each heart measurement is taken relative to the time that the exercise session begins. For yet another example, the weights may be based on a combination of the value of the heart rate measurement and the time at which the heart rate measurement was taken.

Block 510 may output a value for the RHR parameter 440 (e.g., a default RHR, or a statistically determined value for $HR_{min}$ or $HR_{onset}$). In some embodiments, the calorimetry method 400 (FIG. 4) may be able to determine energy expenditure more accurately if the RHR parameter 440 is the user's $HR_{onset}$ instead of the user's $HR_{min}$. In these embodiments, block 610 (or another process) may determine the user's onset heart rate ($HR_{onset}$) and output that value as RHR parameter 440. If $HR_{onset}$ cannot be obtained, or if the obtained $HR_{onset}$ value is determined to be inaccurate, block 510 may output the user's $HR_{min}$ value as the RHR parameter 440 instead.

Figure 7:
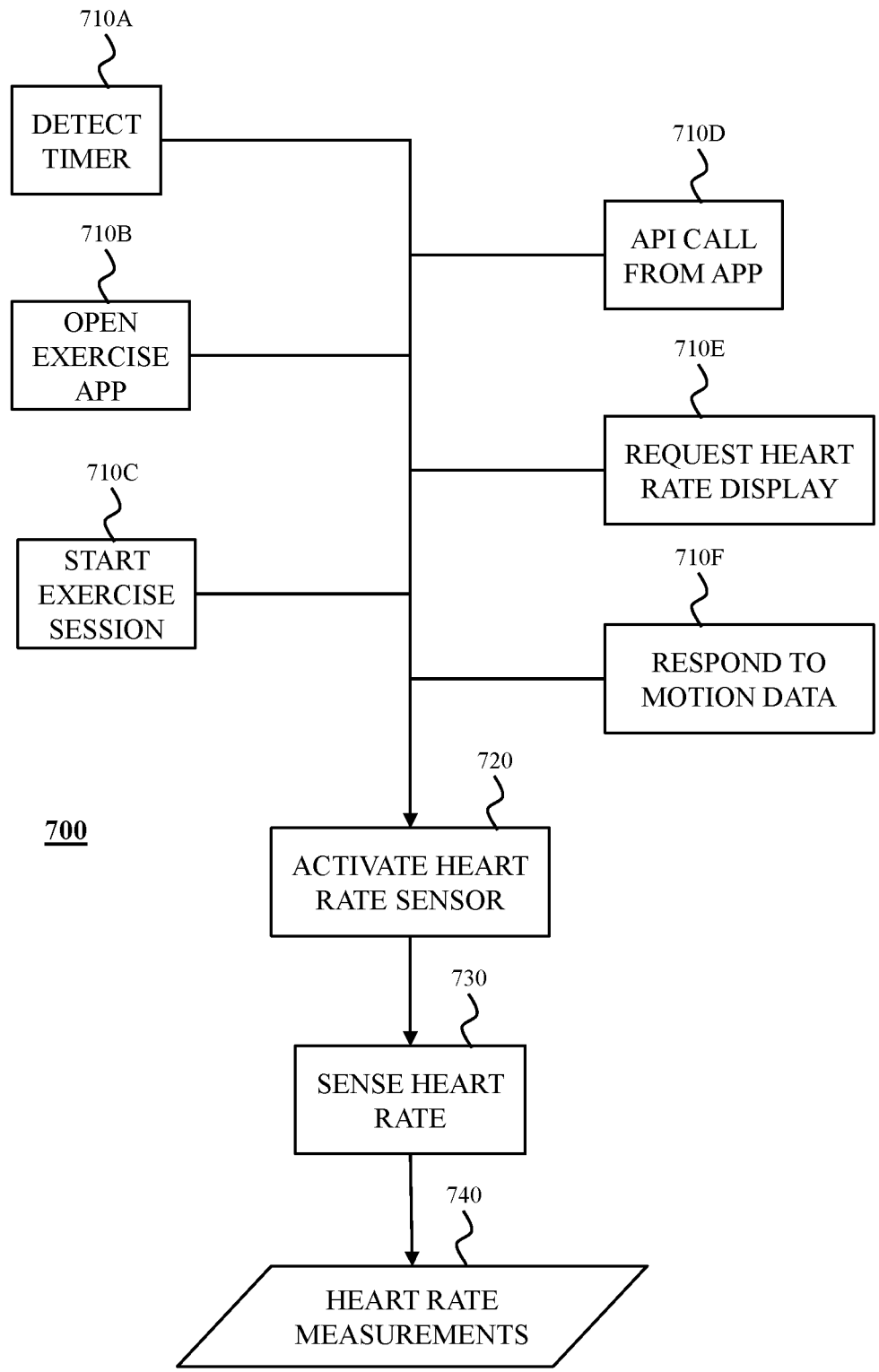
FIG. 7 shows a calibration method for collecting heart rate measurements in accordance with an embodiment of the present disclosure.

FIG. 7 shows a calibration method 700 for collecting heart rate measurements in accordance with an embodiment of the present disclosure. Several techniques for determining biometric parameters for estimating energy expenditure (e.g., $HR_{max}$, RHR, etc.) include collecting heart rate measurements using a heart rate sensor such as heart rate sensing module 210 in fitness tracking device 100. For example, heart rate measurements 540 (FIG. 5) may be collected to determine $HR_{max}$, and heart rate measurements 630 (FIG. 6) may be collected to determine RHR (e.g., $HR_{min}$ or $HR_{onset}$).

Calibration method 700 generally begins when an event occurs that requires or otherwise requests heart rate measurements. Examples of these events are represented as parts of blocks 710A-710F. Calibration method 700 may begin at any block 710A-710F depending on which event may be driving the request for heart rate measurements.

In some embodiments, calibration method 700 may define events specially or exclusively for the purpose of calibrating one or more parameters to use for estimating energy expenditure. In some embodiments described in detail below, calibration method 700 may opportunistically collect heart rate measurements for parameter calibration following events when the heart rate sensor needed to be activated for a different process.

At block 710A, calibration method 700 may begin with a timer event. For example, as described above in relation to collecting heart rate measurements for $HR_{onset}$, a timer may be used to determine when the heart rate sensor should be activated (at block 720).

In other embodiments, other processes of the fitness tracking device 100 or applications running on the fitness tracking device 100 may define a timer event (block 710A). For example, the fitness tracking device 100 may define a timer event that triggers periodically to collect heart rate measurements at regular intervals throughout the day. For example, the timer may be defined to have a period of 10 minutes, 30 minutes, 1 hour, etc.

In some embodiments, this timer may activate a "low-power" mode of the heart rate sensor (e.g., heart rate sensing module 210) at block 720. The low-power mode may use fewer elements (e.g., two LEDs instead of four), or the low-power mode may use lower-power elements (e.g., infrared LEDs instead of colored LEDs). When the heart rate is sensed at block 730 or when the heart rate measurement is collected at output 740, calibration method 700 may take into account whether the heart rate sensing module is operating in a low-power mode. For example, heart rate measurements taken in low-power mode may be less accurate than heart rate measurements taken in a higher-power mode (or a "normal" mode).

In some embodiments, calibration method 700 may begin at block 710B. The fitness tracking device 100 may be configured with a built-in exercise or fitness application. When this app is "opened" or otherwise run, launched, executed, or resumed, the fitness tracking device 100 may proceed to activate the heart rate sensor at block 720 and sense the user's heart rate at block 730. Calibration method 700 may opportunistically collect these heart rate measurements to be used for determining parameters used for estimating energy expenditure.

In some embodiments, calibration method 700 may begin at block 710C. A fitness application (e.g., the built-in exercise application) may signal that the user indicated the start or beginning of an exercise session. This signal may cause the fitness tracking device 100 to proceed to activate the heart rate sensor at block 720 and sense the user's heart rate at block 730. Calibration method 700 may opportunistically collect these heart rate measurements to be used for determining parameters used for estimating energy expenditure.

In some embodiments, calibration method 700 may begin at block 710D. Third-party applications (or "apps") may be downloaded, installed, transferred, or otherwise configured to run on the fitness tracking device. The fitness tracking device 100 may provide an application programming interface (API) or other hook or process within its processor, firmware, operating system, or other built-in software libraries for a third-party application to request heart rate data or information depending on heart rate data. For example, a third-party exercise app may include a "start" function that allows the user to signal the beginning of an exercise session within the third-party exercise app. This signal may cause the fitness tracking device 100 to proceed to activate the heart rate sensor at block 720 and sense the user's heart rate at block 730. Calibration method 700 may opportunistically collect these heart rate measurements to be used for determining parameters used for estimating energy expenditure.

In some embodiments, calibration method 700 may begin at block 710E. The fitness tracking device 100 may display—or respond to an app's request to display—heart rate information, such as the user's current heart rate. This signal may cause the fitness tracking device 100 to proceed to activate the heart rate sensor at block 720 and sense the user's heart rate at block 730. Calibration method 700 may opportunistically collect these heart rate measurements to be used for determining parameters used for estimating energy expenditure.

In some embodiments, calibration method 700 may start at block 710F. The fitness tracking device 100—or an app running on the device—may analyze motion data from the motion sensing module 220 (FIG. 2) in the fitness tracking device 100. The fitness tracking device 100 or the app may determine that heart rate data may be required or may be helpful in light of the analyzed motion data. For example, the fitness tracking device 100 may be able to determine from analyzing motion data the user has been sitting down or has otherwise been at rest for a period of time (e.g., 30 minutes, 1 hour, 2 hours, etc.). The fitness tracking device 100 may determine that the user's heart rate may be at or close to the user's minimum (resting) heart rate (e.g., $HR_{min}$). Calibration method 700 may proceed to activate the heart rate sensor at block 720 and sense the user's heart rate at 730 to collect heart rate measurements 740 that may provide a more accurate value for RHR or $HR_{min}$.

For another example, the fitness tracking device 100 may be able to determine from analyzing motion data that the user's wrist is relatively still, which may allow the heart rate sensing module 210 to obtain a more accurate heart rate measurement. Calibration method 700 may opportunistically collect these heart rate measurements to be used for determining parameters used for estimating energy expenditure.

Other events not shown in FIG. 7 may trigger the beginning of calibration method 700 in addition to the events depicted at blocks 710A-710F. In some embodiments, the fitness tracking device 100 may receive contextual information from other devices indicating that a user is likely seated or otherwise at rest. For example, the contextual information might indicate that the user has been watching a long movie on a computer, television, or other device. Calibration method 700 may proceed to activate the heart rate sensor at block 720 and sense the user's heart rate at 730 to collect heart rate measurements 740 that may provide a more accurate value for RHR or $HR_{min}$.

In some embodiments, the fitness tracking device 100 may analyze location information to determine that a user is likely seated or otherwise at rest. For example, the location information might indicate that the user has been located at a movie theater. Calibration method 700 may proceed to activate the heart rate sensor at block 720 and sense the user's heart rate at 730 to collect heart rate measurements 740 that may provide a more accurate value for RHR or $HR_{min}$.

In some embodiments, the fitness tracking device 100 may analyze content information to determine whether a user is likely to have a relatively higher heart rate due to the content. For example, if the user is watching an action sequence in an action movie, the user may be physiologically aroused and have a relatively higher rate than the user's normal resting heart rate. Calibration method 700 may opportunistically collect these heart rate measurements to be used for determining parameters used for estimating energy expenditure.

In some embodiments, the fitness tracking device 100 may analyze historical information (e.g., from the user's calendar) to determine that the user is likely to start an exercise session at a particular time or place. In anticipation of likely starting an exercise session, calibration method 700 may proceed to activate the heart rate sensor at block 720 and sense the user's heart rate at 730 to collect heart rate measurements 740 that may provide a more accurate value for RHR or $HR_{min}$.

The aforementioned techniques for calibrating and tracking biometric parameters used to estimate energy expenditure are examples and other embodiments may include other techniques that may be used instead of or in addition to the aforementioned techniques. In some embodiments, the fitness tracking device 100 may store historical estimates of these parameters and interpolate or extrapolate new estimates based on the historical estimates in conjunction with heart rate measurements. For example, the fitness tracking device 100 may compute a weighted sum of one or more previous estimates with a value based on more recent measurements to determine the next estimated parameter value.

In some embodiments, parameter values may be inferred by extrapolating from the trajectory of heart rate measurements at the beginning of an exercise session (e.g., during a "ramp-up" or "onset" period), or by extrapolating from the trajectory of heart rate measurements after the exercise session has ended (e.g., during a "cool-down" period).

Additionally, as described above, some embodiments may use values for $HR_{max}$ and $\dot{V}O_2max$ that have been calibrated or otherwise determined in Eq. 4 to determine a value for RHR. Analogously, if values for RHR and $HR_{max}$ have been calibrated or otherwise determined, some embodiments may use them in Eq. 4 to determine a value of $\dot{V}O_2max$. And, if values for RHR and $\dot{V}O_2max$ have been calibrated or otherwise determined, some embodiments may use them in Eq. 4 to determine a value of $HR_{max}$.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

We claim:

1. A method of calibrating a fitness tracking device for calorie estimation for a specific exercise session, the method comprising:
   determining, by a wearable computing device, a start of an exercise session associated with a user of the wearable computing device, the wearable computing device including a processor, a memory, a heart rate sensor, and at least one of a motion sensing module, a display module, and an interface module;
   in response to determining the start of the exercise session, measuring, by the heart rate sensor of the wearable computing device, heart rate data (HR) for a first period of time, the first period of time following the start of the exercise session;
   determining, by the processor of the wearable computing device, an onset heart rate value of the user based on the measured heart rate data, the onset heart rate value associated with a lowest valid heart rate measured during the first period of time, the onset heart rate value being different from a calibrated resting heart rate (RHR) for the user stored in the memory;
   associating, by the processor of the wearable computing device, an RHR parameter of a calorimetry model to the onset heart rate value to calibrate the wearable computing device for the exercise session; and
   estimating, by the processor of the wearable computing device, energy expenditure of the user during a second period of time based on the calorimetry model and a plurality of heart rate measurements (HR) obtained by the wearable computing device during the second period of time, the second period of time associated with a portion of time after the first period of time and prior to an end of the exercise session.

2. The method of claim 1, wherein estimating the energy expenditure further comprises calculating a fraction of heart rate reserve (FHR) based on maximum heart rate ($HR_{max}$), wherein:

$$FHR=(HR_{max}-HR)/(HR_{max}-RHR).$$

3. The method of claim 2, wherein the energy expenditure is proportional to a function $f(FHR)$, wherein $f(FHR)$ is approximately a sigmoidal nonlinearity.

4. The method of claim 3, wherein $f(0)=1$ and $f(1)=0$.

5. The method of claim 2, wherein $HR_{max}$ is based on at least one of:
   an age of the user; and
   at least one of a previously measured heart rate.

6. The method of claim 1, wherein the RHR for the user stored in the memory data comprises a heart rate value based on a maximum oxygen exchange rate of the user ($VO_2max$) and a maximum heart rate of the user ($HR_{max}$), and $VO_2max$ comprises one of a default value or a value previously calibrated by the user.

7. The method of claim 6, wherein the ($HR_{max}$) comprises at least one of:
   a maximum heart rate value of the at least one of a previously measured heart rate;
   a percentile of the at least one of a previously measured heart rate;
   a percentile of the at least one of a previously measured heart rate above a first threshold heart rate value;
   a percentile of the at least one of a previously measured heart rate above a $HR_{max}$ based on the age of the user; and
   a maximum heart rate value being less than a percentage of the $HR_{max}$ based on an age of the user.

8. The method of claim 7, wherein:
the percentile of the at least one of a previously measured heart rate is approximately a $98^{th}$ percentile;
the percentile of the at least one of a previously measured heart rate above a first threshold heart rate value is approximately a $98^{th}$ percentile;
the percentile of the at least one of a previously measured heart rate above a $HR_{max}$ based on the age of the user is approximately a $98^{th}$ percentile; and
the percentage of the $HR_{max}$ based on the age of the user is approximately 110%.

9. The method of claim 1, wherein the calibrated RHR includes at least one of:
a preset value; and
a RHR based on user biometric data.

10. The method of claim 9, wherein the preset RHR comprises at least one of:
a minimum value of a list of RHR values from prior exercise sessions;
a percentile of the list of RHR values from prior exercise sessions; and
a percentile of RHR values in the list below a second threshold heart rate value.

11. The method of claim 10, wherein:
the second threshold heart rate value comprises 90 beats per minute.

12. The method of claim 9, wherein:
the preset value comprises 72 beats per minute; and
the RHR based on user biometric data comprises a heart rate value based on a maximum oxygen exchange rate of the user ($VO_2$max) and a maximum heart rate of the user ($HR_{max}$).

13. The method of claim 1, wherein the first period of time comprises 10 seconds to 1 minute.

14. The method of claim 1, wherein the first period of time is associated with a timer, wherein the timer activates at least one of a low-power mode of heart rate sensing and a high-power mode of heart rate sensing.

15. A system for tracking physiological states and parameters for calorie estimation and configured to be calibrated for a specific exercise session, the system comprising:
a wearable computing device, the wearable computing device including a processor, a memory, a heart rate sensor, and at least one of a motion sensing module, a display module, and an interface module, the wearable computing device configured to:
determine a start of an exercise session associated with a user of the wearable computing device;
in response to determining the start of the exercise session, measure heart rate data (HR) for a first period of time, the first period of time following the start of the exercise session;
determine an onset heart rate value of the user based on the measured heart rate data, the onset heart rate value associated with a lowest valid heart rate measured during the first period of time, the onset heart rate value being different from a calibrated resting heart rate (RHR) for the user stored in the memory;
associate an RHR parameter of a calorimetry model to the onset heart rate value to calibrate the wearable computing device for the exercise session; and
estimate energy expenditure of the user during a second period of time based on the calorimetry model and a plurality of heart rate measurements (HR) obtained by the wearable computing device during the second period of time, the second period of time associated with a portion of time after the first period of time and prior to an end of the exercise session.

16. The system of claim 15, wherein estimating the energy expenditure further comprises calculating a fraction of heart rate reserve (FHR) based on maximum heart rate ($HR_{max}$), wherein:

$$FHR=(HR_{max}-HR)/(HR_{max}-RHR).$$

17. The system of claim 16, wherein $HR_{max}$ is based on at least one of:
an age of the user; and
at least one of a previously measured heart rate.

18. The system of claim 17, wherein the at least one of a previously measured heart rate comprises at least one of:
a maximum heart rate value of the at least one of a previously measured heart rate;
a percentile of the at least one of a previously measured heart rate;
a percentile of the at least one of a previously measured heart rate above a first threshold heart rate value;
a percentile of the at least one of a previously measured heart rate above a $HR_{max}$ based on the age of the user; and
a maximum heart rate value being less than a percentage of the $HR_{max}$ based on the age of the user.

19. The system of claim 15, wherein the calibrated RHR includes at least one of:
a preset value; and
a RHR based on user biometric data.

20. The system of claim 19, wherein the preset RHR comprises at least one of:
a minimum value of a list of RHR values from prior exercise sessions;
a percentile of the list of RHR values from prior exercise sessions; and
a percentile of RHR values in the list below a second threshold heart rate value.

* * * * *